(12) United States Patent
Biddle et al.

(10) Patent No.: US 7,834,231 B2
(45) Date of Patent: Nov. 16, 2010

(54) LOW PROFILE CHEST SEAL

(75) Inventors: John R. Biddle, Monticello, IN (US);
Robert H. Harder, Bena, VA (US);
Charles T. Bolin, Stafford, VA (US)

(73) Assignee: H & H Associates, Inc., Ordinary, VA (US)

( * ) Notice: Subject to any disclaimer, the term of this patent is extended or adjusted under 35 U.S.C. 154(b) by 820 days.

(21) Appl. No.: 11/723,380

(22) Filed: Mar. 19, 2007

(65) Prior Publication Data
US 2008/0234726 A1    Sep. 25, 2008

(51) Int. Cl.
*A61F 13/00* (2006.01)
(52) U.S. Cl. .......................................... 602/41; 602/42
(58) Field of Classification Search .................. 128/887, 128/888, 889; 604/122, 126, 304, 307; 602/41–56
See application file for complete search history.

(56) References Cited

U.S. PATENT DOCUMENTS

| 4,465,062 | A | * | 8/1984 | Versaggi et al. ............. 128/897 |
| 4,717,382 | A | * | 1/1988 | Clemens et al. ............. 604/122 |
| 5,478,333 | A | | 12/1995 | Asherman, Jr. |
| 7,429,687 | B2 | * | 9/2008 | Kauth et al. .................. 602/58 |
| 7,615,674 | B2 | * | 11/2009 | Asherman ..................... 602/58 |

OTHER PUBLICATIONS

Brochure; "An Enhanced One-way Valve"; Pacific Bag inc.; No date; 2 pages.

* cited by examiner

*Primary Examiner*—Michael A. Brown
(74) *Attorney, Agent, or Firm*—Nixon & Vanderhye PC

(57) ABSTRACT

A chest seal for treating an open pneumothorax that is low profile and thus unobtrusive so that the chest seal can be effectively maintained in position to seal a chest wound while allowing the pleural cavity to vent.

20 Claims, 4 Drawing Sheets

LOW PROFILE CHEST SEAL

BACKGROUND OF THE INVENTION

When an individual suffers a puncture wound to the chest, such as from being shot or stabbed, the wound often penetrates into the chest cavity so as to puncture the parietal pleura, visceral pleura, and sometimes even the lungs. Such a wound allows air to flow freely into the chest cavity and pleural space.

An open pneumothorax is a condition wherein air penetrates into the pleural space between the lung(s) and the chest wall through a wound hole. When a patient has an open pneumothorax, the normal mechanism by which the lungs expand is inhibited or lost. Consequently, the affected lung will not expand when the patient inhales and respiratory distress ensues. The severity of an open pneumothorax can be minimized by sealing the open wound. However, already trapped air is not allowed to escape from the pleural space.

U.S. Pat. No. 5,478,333 discloses a chest seal having a duck bill valve that prevents air from entering the pleural space while allowing already trapped air to escape. The duck bill valve is attached to a cylindrical section of duct that projects from the body attached flange of the chest seal. The cylindrical section allows the chest seal to be used as a conduit for a catheter if a severe tension pneumothorax or collapsed lung is to be treated with an invasive procedure and/or allows a suction device to be inserted if a hemothorax or collapsed lung is to be treated without invasive procedures. However, the cylindrical section and elongated duck bill valve are obtrusive. The dangling free end of the valve may be inadvertently caught and pulled by medical personnel or equipment so as to dislodge the chest seal and/or pressure from medical equipment or other dressings may prevent the duck bill valve from venting the chest wound. In fact the '333 patent explains that the one-way valve may not open to allow air to be expelled if the patient is lying on the valve.

Thus, a need remains for a low profile chest seal that ensures effective venting of the pleural cavity while sealing a chest wound against air entry, without risk of being dislodged during treatment of the patient, particularly when invasive procedures or other auxiliary procedures are not required.

BRIEF DESCRIPTION OF THE INVENTION

The invention provides a chest seal for treating an open pneumothorax that is low profile and thus unobtrusive so that the chest seal can be effectively maintained in position to seal a chest wound while allowing the pleural cavity to vent.

Thus, the invention may be embodied in a chest seal comprising: a flexible flange body having a top side surface and a bottom side surface, said flange body having at least one opening defined therethrough in a central portion thereof; a biocompatible adhesive disposed on said bottom surface of said flexible flange body and at least one one-way valve secured with respect to said upper surface of said flange body so as to overlie a respective at least one said central opening, said one-way valve comprising a valve body having a peripheral wall, a passage defined therethrough, and a sealing element disposed in said valve body so as to selectively seat to seal said passage to preclude air flow in one direction through said valve body and so as to be selectively unseated to allow flow through said valve body in the opposite direction, whereby when the flange body is adhered to the skin of a patient with said at least one central opening generally overlying a chest wound, air is allowed to escape from the chest wound through the one-way valve whereas air flow into the chest wound is precluded.

The invention may also be embodied in a method of treating an open pneumothorax comprising: providing a chest seal comprising a flexible flange body having a top side surface and a bottom side surface, said flange body having at least one opening defined therethrough in a central portion thereof, a biocompatible adhesive disposed on said bottom surface of said flexible flange body, and a one-way valve secured with respect to said upper surface of said flange body so as to overlie a respective at least one said central opening, said one-way valve comprising a valve body having a peripheral wall, a passage defined therethrough and a sealing element disposed in said valve body so as to selectively seat to seal said passage to preclude air flow in one direction through said valve body and so as to be selectively unseated to allow flow through said valve body in the opposite direction; wiping the patient's skin in an area around the chest wound; applying the chest seal to the patient's skin with at least one said central opening overlying the chest wound; and pressing to adhere the adhesive to patient's skin around and about the chest wound, whereby air is allowed to escape from the chest wound through the one-way valve whereas air flow into the chest wound is precluded.

DETAILED DESCRIPTION OF THE INVENTION

Figure 1:
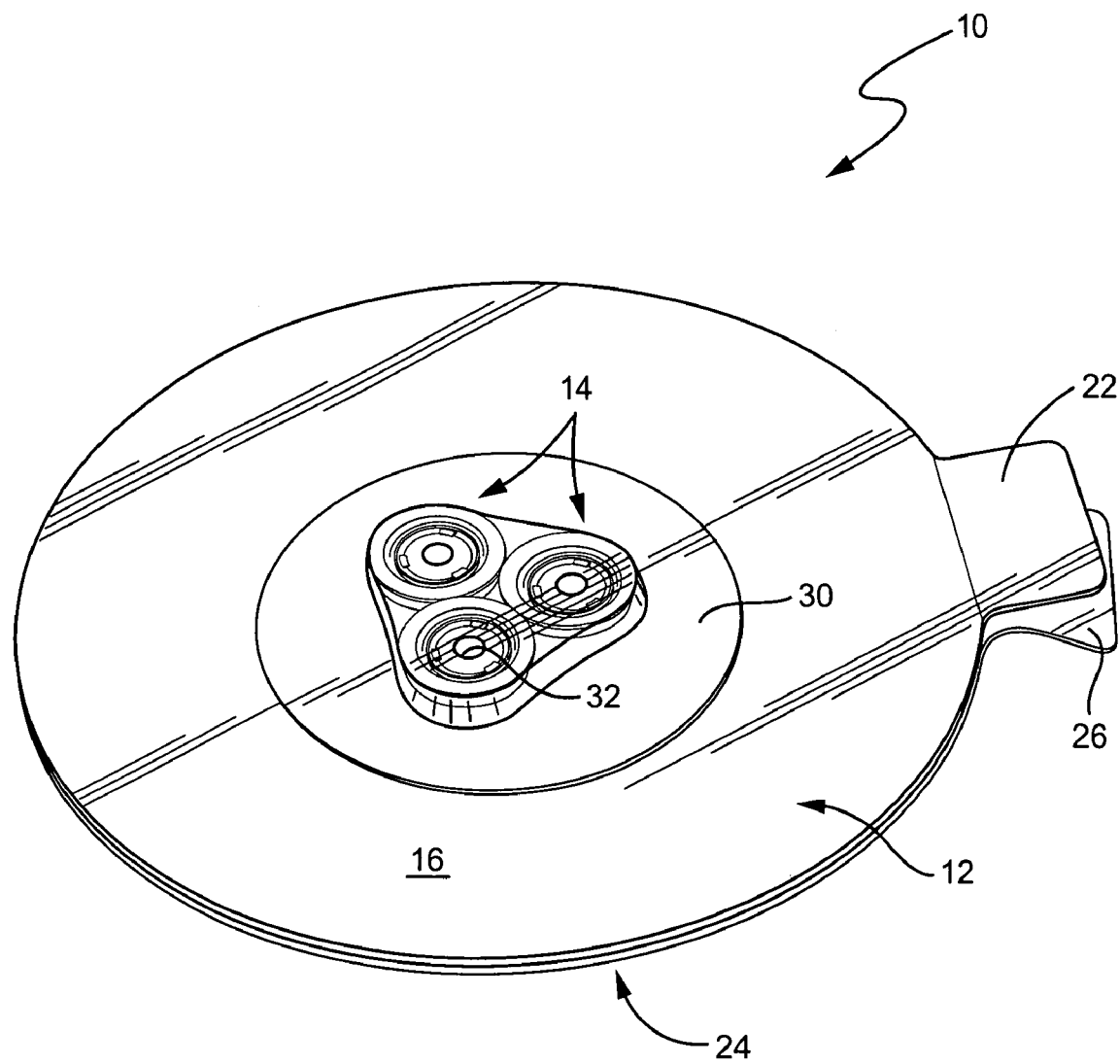
FIG. 1 is a perspective view of a chest seal embodying the invention with the backing material shown partly peeled away.

A chest seal 10 embodying the invention is comprised of a flange like main body 12 (hereinafter "flange body") and at least one generally centrally disposed one-way valve 14. The flange body 12 has a top side 16 and an under side 18 on which a biocompatible adhesive 20 is disposed for securing the flange body to a patient's skin. Suitable adhesives for adhering the flange body to the patient's skin include hydro gel, acrylic, silicone gel, silicone PSA or hydrocolloid. In the illustrated example embodiment, no adhesive is provided on a release tab projection 22 which is grasped to remove the chest seal flange body 12 from the patient's skin when the chest seal is to be removed.

Figure 3:
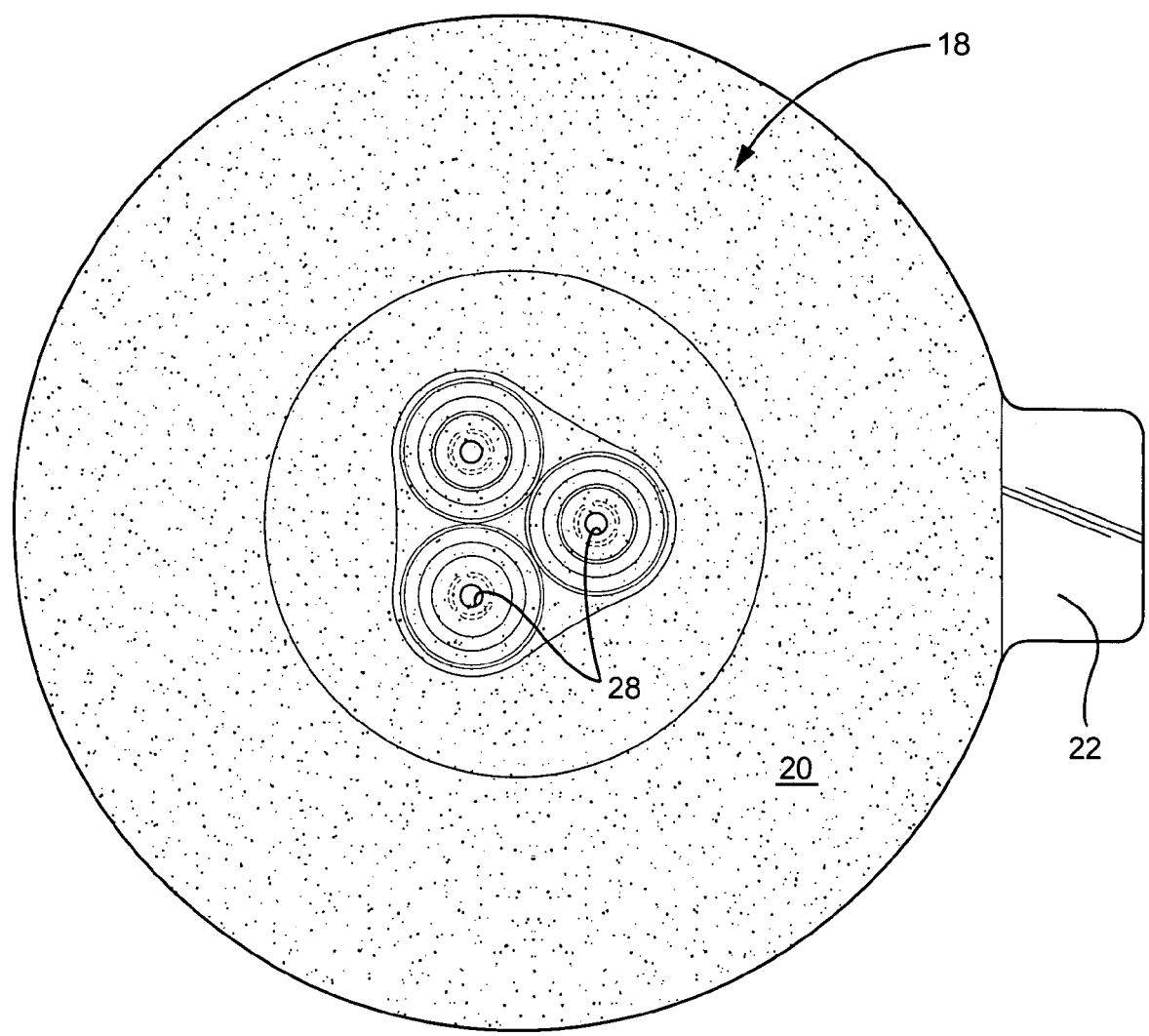
FIG. 3 is a bottom plan view of the chest seal of FIG. 1 with the peel-off backing removed.

Referring to FIGS. 1 and 3, a peel-off backing 24 is disposed to cover the adhesive 20 on the underside of the flange body 12. The peel-off backing 24 also includes a finger pull 26, which in the illustrated embodiment corresponds in location to the tab projection 22 of the flange body 12. While typically the tab 22 will be of the same size and configuration as the finger pull 26 of the flange body, it is to be understood that these parts do not have to correspond in size and shape.

The flange body 12 is constructed of a pliable, flexible material so that the chest seal 10 can be applied to adhere to any contour of the patient's body. In this regard, it is important for the chest seal to conform to the patient's outer chest wall to effectively seal about the chest wound to block air inflow. In an example embodiment the flange body 12 is formed from 10 mil urethane. Other suitable body materials may include other thicknesses or polyurethane, polyethylene, polypropylene, nylon, or polyolefin. These can be in film or foam. In the illustrated example embodiment, the chest seal is generally circular and has a diameter of about 5 to 6 inches, although the shape of the flange body is not critical and a square flange body or flange body of other shape may be provided without departing from the invention.

As noted above, at least one one-way valve 14 is operatively coupled to the flange body 12. In the illustrated example embodiment, at least one opening 28 is defined through the flange body 12 in general alignment with each one-way valve 14 so that when the flange body is adhered to the patient's outer chest wall, the one-way valve is in flow communication with the patient's chest wound through the opening(s) 28. In this way air is allowed to escape from the chest wound through the one-way valve, but the one-way valve closes so as to block air in flow into the chest cavity. In the illustrated example embodiment, three one-way valves 14 are symmetrically disposed centrally of the flange body 12, each aligned with a respective opening 28 through the flange body, to ensure effective venting of the wound even if the flange body is not precisely placed.

Figure 2:
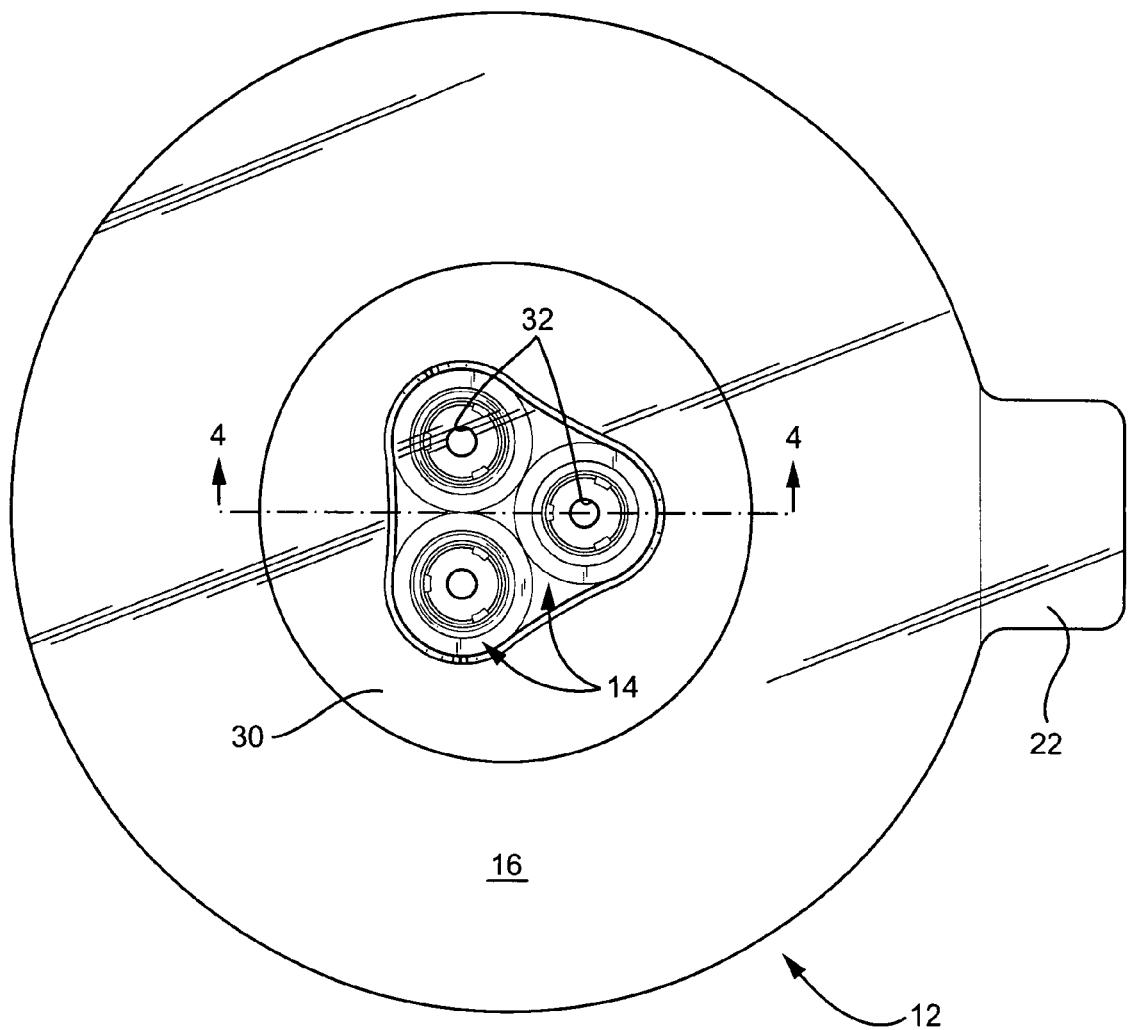
FIG. 2 is a top plan view of a chest seal according to an example embodiment of the invention.

In the illustrated example embodiment, the one-way valve(s) 14 are secured or mounted to the flange body 12 by disposing a sealing membrane 30 to overlie the valve(s) 14 and adhere to the top side 16 of the flange body 12. As illustrated in FIGS. 1 and 2, at least one opening 32 is defined through the mounting membrane in general alignment with each one-way valve 14 to complete the air circuit through the chest seal 10. The valves may be attached using a pressure sensitive adhesive, RF welding and/or heat sealed to the flange body. Of course the number of openings 32 in the sealing membrane and size of the membrane will depend upon the number, size and placement of the one-way valves 14.

Figure 4:
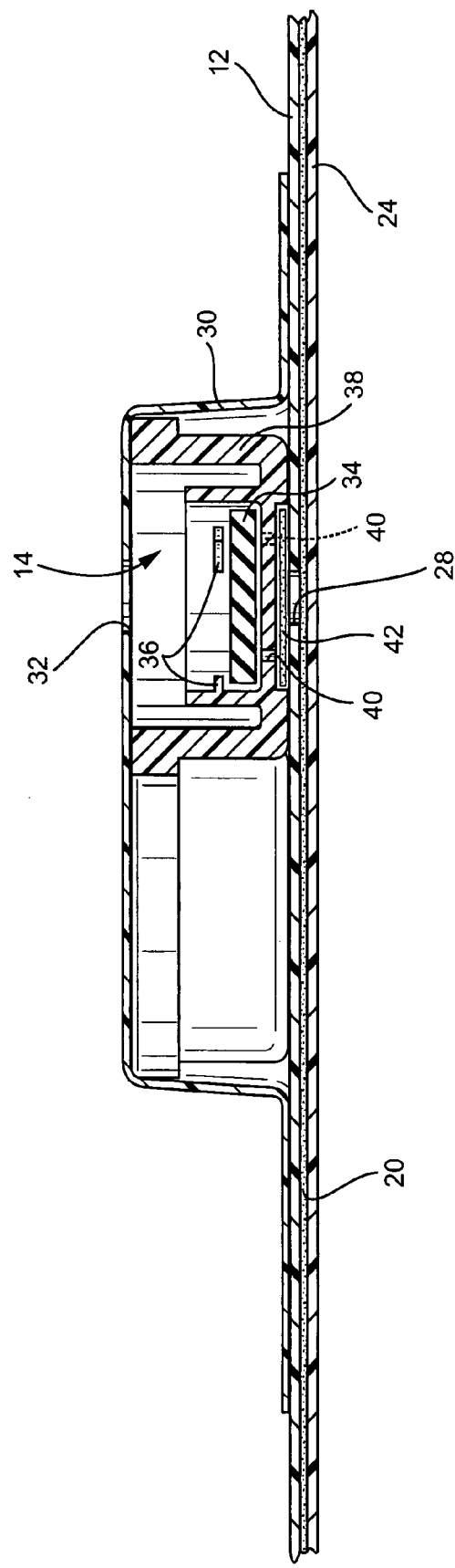
FIG. 4 is a cross-sectional view taken along lines 4-4 of FIG. 2.

Referring to FIGS. 1 and 4, in an example embodiment, the one-way valve is a Pacific Bag Inc. (PBi) one-way degassing valve, which is a very efficient single-part valve. In this regard, the mounting membrane 30 serves as a cap for the valve 14 and a sealing disk 34 for blocking air flow in one direction through the valve is held in place with three projections 36 that are incorporated directly into the valve body 38 instead of in a cap or other auxiliary component. As will be appreciated, the mounting membrane 30 and the integrally formed valve body 38 contribute to the generally low profile of the valve 14 consistent with the objects of the invention. In an example embodiment, the valve body 38 is molded plastic, such as polyethylene, polypropylene or nylon. Stainless or aluminum could be used if it is attached via a pressure sensitive adhesive, as one could produce a low profile valve in this configuration made of a metal. The sealing disk 34 is formed from an elastomeric material, such as natural rubber, that can be pushed past the projections 36 during assembly and can resiliently seal against the valve body 38 to block air flow through passage(s) 40 into the chest cavity. In the embodiment illustrated in FIG. 4, the sealing disk seats on the bottom wall of the valve body 38 which thus serves as the valve seat of the valve body. Moreover, in the illustrated embodiment, the valve body is configured and disposed such that its bottom wall is generally parallel to the plane of the flange body 12. Although the provision of a sealing component in the form of a sealing disk 34 is presently preferred, it is to be appreciated that sealing components having other configurations, such as a ball or flap may be disposed in the valve body 38 as an alternative. In the illustrated example, furthermore, a filter membrane 42 is seated between the valve body and the flange body. The filter membrane, also referred to as a scrim, is provided to keep clots or debris from entering the one-way valve. In an example embodiment a polyester filter is provided, but other materials, such as nylon, polyethylene, polypropylene and fiberglass could be used.

As mentioned above, the single part design of the PBi valve makes it particularly low profile, which allows it to be readily incorporated in the chest seal of the invention, individually or, as in the illustrated embodiment, with two or more valves together defining a valving system.

To use the chest seal 10 of the invention in a non-invasive procedure, the patient's skin around the wound hole is wiped clean of blood and sweat to ensure appropriate adhesion of the chest seal 10. The peel off backing 24 is removed by grasping the finger pull 26 and peeling away the backing to expose the adhesive 20 disposed on the under side 18 of the flange body 12. The chest seal is then positioned over the wound hole so that the one-way valve(s) 14 generally overlie the wound hole. The flange body 12 is then pressed against the patient's skin to ensure that the chest seal has adhered completely to the patient's skin, so that air released from the wound will exit via the one-way valve(s) 14 whereas air inflow will be blocked by the adhesive attachment on the one hand and by the one-way valve(s) on the other hand.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A chest seal comprising:
   a flexible flange body having a top side surface and a bottom side surface, said flange body having at least one opening defined therethrough in a central portion thereof;
   a biocompatible adhesive disposed on said bottom surface of said flexible flange body; and
   at least one one-way valve secured with respect to said upper surface of said flange body so as to overlie a respective at least one said central opening, said one-way valve comprising a valve body having a peripheral wall, a passage defined therethrough, a valve seat, and a sealing element disposed in said valve body so as to selectively seat on said valve seat to seal said passage to preclude air flow in one direction through said valve body toward the at least one opening in the flange body and so as to be selectively unseated from said valve seat to allow air flow through said valve body in a direction opposite the one direction, said sealing element comprising an elastomeric sealing element, said valve seat being defined on a transverse wall of said valve body that is disposed in a plane that is substantially parallel to a plane of said flange body,
   whereby when the flange body is adhered to the skin of a patient with said at least one central opening generally overlying a chest wound, air is allowed to escape from the chest wound through the one-way valve whereas air flow into the chest wound is precluded.

2. A chest seal as in claim 1, wherein said one-way valve is mounted to said upper surface of said flange body with a mounting membrane disposed to overlie said valve and having at least one opening aligned with said valve body for air to escape from the one-way valve through the mounting membrane.

3. A chest seal as in claim 2, wherein said mounting membrane is adhesively secured to said upper surface of said flange body.

4. A chest seal as in claim 1, wherein there are a plurality of one-way valves secured with respect to said upper surface.

5. A chest seal as in claim 4, wherein there are three one-way valves.

6. A chest seal as in claim 1, wherein said sealing element comprises an elastomeric sealing disk that is free-floating within said valve body between the seated and unseated positions thereof.

7. A chest seal as in claim 1, further comprising a peel-off backing for covering and protecting said adhesive prior to application of the chest seal.

8. A chest seal as in claim 1, further comprising a filter component disposed between aid valve body and said flange body.

9. A chest seal comprising:
a flexible flange body having a top side surface and a bottom side surface, said flange body having at least one opening defined therethrough in a central portion thereof;
a biocompatible adhesive disposed on said bottom surface of said flexible flange body and at least one one-way valve secured with respect to said upper surface of said flange body so as to overlie a respective at least one said central opening, said one-way valve comprising a valve body having a peripheral wall, a passage defined therethrough, and a sealing element disposed in said valve body so as to selectively seat to seal said passage to preclude air flow in one direction through said valve body and so as to be selectively unseated to allow flow through said valve body in the opposite direction, whereby when the flange body is adhered to the skin of a patient with said at least one central opening generally overlying a chest wound, air is allowed to escape from the chest wound through the one-way valve whereas air flow into the chest wound is precluded, and
further comprising a filter component disposed between said valve body and said flange body.

10. A chest seal as in claim 9, wherein said one-way valve is mounted to said upper surface of said flange body with a mounting membrane disposed to overlie said valve and having at least one opening aligned with said valve body for air to escape from the one-way valve through the mounting membrane.

11. A chest seal as in claim 9, wherein there are a plurality of one-way valves secured with respect to said upper surface.

12. A chest seal as in claim 9, wherein said sealing element comprises an elastomeric sealing disk that seats and unseats from a valve seat defined on a transverse wall of said valve body, said transverse wall being disposed in a plane that is substantially in parallel to a plane of said flange body.

13. A method of treating an open pneumothorax comprising:
providing a chest seal comprising a flexible flange body having a top side surface and a bottom side surface, said flange body having at least one opening defined therethrough in a central portion thereof, a biocompatible adhesive disposed on said bottom surface of said flexible flange body, and a one-way valve secured with respect to said upper surface of said flange body so as to overlie a respective at least one said central opening, said one-way valve comprising a valve body having a peripheral wall, a passage defined therethrough, a valve seat, and a sealing element disposed in said valve body so as to selectively seat on said valve seat to seal said passage to preclude air flow in one direction through said valve body toward the central opening and so as to be selectively unseated from said valve seat to allow air flow through said valve body in a direction opposite the one direction, said sealing element comprising an elastomeric sealing element, said valve seat being defined on a transverse wall of said valve body that is disposed in a plane that is substantially in parallel to a plane of said flange body;
wiping the patient's skin in an area around the chest wound;
applying the chest seal to the patient's skin with at least one said central opening overlying the chest wound; and
pressing to adhere the adhesive to patient's skin around and about the chest wound, whereby air is allowed to escape from the chest wound through the one-way valve whereas air flow into the chest wound is precluded.

14. A method as in claim 13, wherein said one-way valve is mounted to said upper surface of said flange body with a mounting membrane disposed to overlie said valve and having at least one opening aligned with said. valve body for air to escape from the one-way valve through the mounting membrane.

15. A method as in claim 14, wherein said mounting membrane is adhesively secured to said upper surface of said flange body.

16. A method as in claim 13, wherein there are a plurality of one-way valves secured with respect to said upper surface.

17. A method as in claim 16, wherein there are three one-way valves.

18. A method as in claim 13, wherein said sealing element comprises an elastomeric sealing disk that is free-floating within said valve body between the seated and unseated positions thereof.

19. A method as in claim 13, wherein the chest seal further comprises a peel-off backing for covering and protecting said adhesive prior to application of the chest seal, and wherein the method further comprises removing said peel-off backing before said applying step.

20. A method as in claim 13, further comprising a filter component disposed between said valve body and said flange body.

* * * * *